United States Patent
Liu et al.

(10) Patent No.: US 10,421,852 B2
(45) Date of Patent: Sep. 24, 2019

(54) PREPARATION METHOD OF NEW-TYPE NANOPARTICLES FOR LOADING EMODIN

(71) Applicant: Guangdong Provincial Hospital of TCM, Guangzhou (CN)

(72) Inventors: Xusheng Liu, Guangzhou (CN); Qizhan Lin, Guangzhou (CN); Chuan Zou, Guangzhou (CN); Fuhua Lu, Guangzhou (CN); Zhaoyu Lu, Guangzhou (CN); Xiuqing Wu, Guangzhou (CN); Yuchi Wu, Guangzhou (CN); Chunlan Ji, Guangzhou (CN)

(73) Assignee: GUANGDONG PROVINCIAL HOSPITAL OF TCM, Guangzhou (CN)

( * ) Notice: Subject to any disclaimer, the term of this patent is extended or adjusted under 35 U.S.C. 154(b) by 135 days.

(21) Appl. No.: 15/815,501

(22) Filed: Nov. 16, 2017

(65) Prior Publication Data
US 2018/0258257 A1 Sep. 13, 2018

(30) Foreign Application Priority Data
Mar. 8, 2017 (CN) .......................... 2017 1 0133054

(51) Int. Cl.
| | |
|---|---|
| C08K 5/378 | (2006.01) |
| C08B 37/08 | (2006.01) |
| C08G 63/42 | (2006.01) |
| C08L 67/04 | (2006.01) |
| A61K 9/51 | (2006.01) |
| C08L 5/08 | (2006.01) |
| C08G 63/664 | (2006.01) |
| C08G 63/91 | (2006.01) |
| G01N 21/35 | (2014.01) |
| B82Y 5/00 | (2011.01) |
| G01R 33/46 | (2006.01) |

(52) U.S. Cl.
CPC ............ *C08K 5/378* (2013.01); *A61K 9/5146* (2013.01); *A61K 9/5153* (2013.01); *A61K 9/5161* (2013.01); *A61K 9/5192* (2013.01); *C08B 37/003* (2013.01); *C08G 63/42* (2013.01); *C08G 63/664* (2013.01); *C08G 63/912* (2013.01); *C08L 5/08* (2013.01); *C08L 67/04* (2013.01); *B82Y 5/00* (2013.01); *C08L 2203/02* (2013.01); *G01N 2021/3595* (2013.01); *G01R 33/46* (2013.01)

(58) Field of Classification Search
CPC ........ C08K 5/378; C08B 37/08; C08G 63/42; C08L 67/04; A61K 9/51
USPC ......................................................... 524/93
See application file for complete search history.

(56) References Cited

U.S. PATENT DOCUMENTS

2017/0281559 A1* 10/2017 Chaudhary .......... A61K 9/5146

\* cited by examiner

*Primary Examiner* — Deve E Valdez
(74) *Attorney, Agent, or Firm* — Innovation Capital Law Group, LLP; Vic Lin

(57) ABSTRACT

The invention relates to a preparation method of new-type nanoparticles for loading emodin, which comprises: using L.A, mPEG and stannous iso caprylate to synthesize a first intermediate product; using the first intermediate product, butanedioic anhydride and 4-dimethylaminopyridine to synthesize a second intermediate product; using the second intermediate product, 1-ethyl-(3-dimethylamino propyl) carbodiimide hydrochloride, N-hydroxysuccinimide and chitosan to synthesize a third intermediate product; using the third intermediate product and sodium periodate to synthesize a fourth intermediate product; using the fourth intermediate product and 5-amino-2-mercapto benzimidazole to synthesize the new-type thiolated nanoparticles. The nanoparticles loaded with emodin are used for intestinal tract dose, which may enhance the nanoparticles' adhesion ability, prolong residence time of drugs on mucosal membranes, and facilitate sustained-release of drug molecules. The encapsulation efficiency after loading drugs is no less than 83.6%, the drug loading capacity is no less than 3.89%, and good water solubility and biological degradability are provided.

7 Claims, 2 Drawing Sheets

PREPARATION METHOD OF NEW-TYPE NANOPARTICLES FOR LOADING EMODIN

TECHNICAL FIELD

The present invention relates to the technical field of bioadhesive drug carriers, and more particularly, it concerns a method of making new-type nanoparticles for loading emodin.

BACKGROUND

Chitosan (CS), also called 2-amino-2-deoxy-β-D-glucose, was the deacetyl chitin (2-acetylamino-2-deoxy-β-D-glucose). Chitin, also called crab shell element, chellotin, chitinous substance, tunicin, etc., is a natural linear polysaccharide and is a primary component of the exoskeletons of crustaceans, which also exists in cell walls of lower plants such as fungi and alga. Since the chitosan contains non toxic, and has good biocompatibility and biodegradability, it has been widely used in the field of medical auxiliary material. The chitosan can form hydrogen bond and electrostatic interaction with the mucosal membrane protein, and has good bioadhesive properties, but the adhesion ability based on the non covalent bond does not guarantee the sustained release of drugs at the targeted part, which limits the application of the chitosan. However, after thiolation of chitosan, the adhesion ability of chitosan is significantly enhanced. This is because that thiomers can form disulfide bonds with mucosal layers, and generate specific binding with the cysteine-rich subdomains of the mucoproteins.

However, the use of thiolated polymers as hydrophobic drug carriers is not ideal. This is because that the reaction between the thiolated polymers and the hydrophobic drug molecules is very weak, thus it usually causes quick release, unsustainable release and bad encapsulation efficiency of the drug.

SUMMARY

A technical problem to be solved by the present invention is to provide a preparation method of new-type nanoparticles for loading emodin to solve the above defects of the prior art. For this new-type thiolated nanoparticles, thiolated mPEG-PLA-CS-MBI nanoparticles are synthesized by means of stepwise synthesis, during the synthetic process, hydrophilia methoxy polyethylene glycol (mPEG) finally forms an mPEG-PLA-CS polymer with polylactic acid (PLA) and chitosan (CS), and on this basis, the polymer is sulfhydrylated through 5-amino-2-mercapto benzimidazole (MBI) to form a thiolated polymer (mPEG-PLA-CS-MBI) eventually. The thiolated polymer (mPEG-PLA-CS-MBI) can load hydrophobic drugs such as emodin to use as sustained-release drugs. The thiolated polymer forms a disulfide bond to adhere to the surface of a mucosal membrane through thiol oxidation, which gives enhanced adhesive properties to the nanoparticles to prolong the residence time of the drugs on the mucosal membrane, and it facilitates the sustained release of drug molecules. Meanwhile, after the modified chitosan is combined with the drugs to form a nano-composite, the mPEG may form a core-shell structure micelle on the surface of the composite to prevent the nano-composite from being identified and cleared by the reticuloendothelial system (RES), so that the prepared particles have the surface stabilization effect, which can facilitate the purpose of long circulation of the composite particles in vivo.

To solve the technical problem above, an approach adopted in the present invention is as follows: a preparation method of new-type nanoparticles for loading emodin is characterized in that the method comprises the following steps:

step 1: dissolving 5 g-20 g of L-Lactide, 2 g-10 g of methoxy polyethylene glycol and 0.2 g-1 g of stannous iso caprylate in 20 mL of dichloromethane, placing the mixture into glacial diethyl ether to deposit for three times after reacting for 18 h at 130° C., and then drying the mixture for 3 d at 40° C. under vacuum condition to obtain a first intermediate product mPEG-PLA-OH;

step 2: dissolving 10 g of the first intermediate product mPEG-PLA-OH prepared in step 1, 2 g of butanedioic anhydride and 1.2 g of 4-dimethylaminopyridine in 100 mL of chloroform, adding 2 mL of triethylamine after evenly stirring the mixture, placing the mixture in diethyl ether to deposit for three times after reacting for 3 d at room temperature, obtaining filter residues through filtration, and drying the filter residues for 3 d at 40° C. in vacuum condition to finally obtain a second intermediate product mPEG-PLA-COOH;

step 3: dissolving 2.5 g of the second intermediate product mPEG-PLA-COOH prepared in step 2 in 40 mL of dichloromethane, then adding 0.7 g of 1-ethyl-(3-dimethylamino propyl) carbodiimide hydrochloride and 0.7 g of N-hydroxysuccinimide to react for 24 h at room temperature, dissolving the mixture in dimethyl sulfoxide solution after rotary evaporation, then adding the mixture in 60 mL of dimethyl sulfoxide added with chitosan to react for 24 h, dialyzing for 3 d, and performing a freeze-drying process to obtain a third intermediate product mPEG-PLA-CS; wherein the additive amount of the chitosan is between 0.1 g-1 g, with boundary values included, and the deacetylation degree is 85%;

step 4: dissolving 0.5 g of the third intermediate product mPEG-PLA-CS prepared in step 3 in 140 mL of water, then adding 0.3 g of sodium periodate solution, after incubating for 2 h at room temperature, adding 300 μL of ethylene glycol to react for 2 h at room temperature, dialyzing for 3 d, and performing the process of freeze-drying to obtain a fourth intermediate product mPEG-PLA-CS-CHO, keeping the fourth intermediate product at 4° C., wherein the concentration of the sodium periodate solution is 2.14 g/L; and step 5: dissolving 0.2 g-1 g of 5-amino-2-mercapto benzimidazole and 0.2 g of the fourth intermediate product mPEG-PLA-CS-CHO prepared in step 4 in 40 mL of dimethyl sulfoxide solution and incubating for 2 h at room temperature, then adding 0.2 g-2 g of sodium cyanoborohydride to react for 24 h to 72 h at room temperature, dialyzing for 3 d, and performing the process of freeze-drying to obtain thiolated mPEG-PLA-CS-MBI nanoparticles used for loading the emodin and keeping the nanoparticles at 4° C.;

both the dimethyl sulfoxide solution in step 3 and the dimethyl sulfoxide solution in step 5 being prepared by mixing dimethyl sulfoxide with water according to a volume ratio of 1:1.

The preparation method of new-type nanoparticles for loading emodin above is characterized in that the average molecular weight of the methoxy polyethylene glycol in step 1 is between 1000 to 4000, with boundary values included.

The preparation method of new-type nanoparticles for loading emodin above is characterized in that the mass of the L-Lactide in step 1 is 14.4 g, the mass of the methoxy polyethylene glycol is 7.6 g, and the mass of the stannous iso caprylate is 0.2 g.

The preparation method of new-type nanoparticles for loading emodin above is characterized in that the additive amount of the chitosan in step 3 is 0.5 g.

The preparation method of new-type nanoparticles for loading emodin above is characterized in that the mass of the 5-amino-2-mercapto benzimidazole in step 5 is 0.5 g.

The preparation method of new-type nanoparticles for loading emodin above is characterized in that the mass of the sodium cyanoborohydride added in step 5 is 0.2 g.

The preparation method of new-type nanoparticles for loading emodin above is characterized in that the reaction time in step 5 is 48 h.

Compared with the prior art, the present invention has the following advantages.

1. The thiolated mPEG-PLA-CS-MBI nanoparticles are synthesized via the stepwise synthesis method according to the present invention, the hydrophilia methoxy polyethylene glycol (mPEG) finally forms the mPEG-PLA-CS polymer with the polylactic acid (PLA) and the chitosan (CS) in the synthetic process, and on this basis, the polymer is thiolated through 5-amino-2-mercapto benzimidazole (MBI), thus the thiolated polymer (mPEG-PLA-CS-MBI) is formed eventually. The thiolated polymer forms disulfide bonds through thiol oxidation to adhere to the surface of the mucosal membrane, which gives enhanced adhesion ability to the new-type thiolated nanoparticles and prolongs residence time of the drugs on the mucosal membrane, thus it facilitates the sustained release of the drug molecules. Meanwhile, after the modified chitosan is combined with the drugs to form the nano-composite, the methoxy polyethylene glycol may form micelles with core-shell structure on the surface of the composite to prevent the nano-composite from being identified and cleared by the reticuloendothelial system (RES), so that the prepared new-type thiolated nanoparticles have the effect of surface stabilization, which can promote the long circulation of the composite particles in vivo.

2. The encapsulation efficiency of the drugs is no less than 83.6% when using the thiolated nanoparticles prepared according to the present invention to load emodin, the drug loading capacity is no less than 3.89%, and the drug has good water solubility and biological degradability.

3. The thiolated mPEG-PLA-CS-MBI nanoparticles prepared according to the present invention can not only be used for loading emodin, but also may be applied to load hydrophobic drugs such as emodin to use as sustained-release drug carriers.

The technical solution of the present invention will be further described in details through drawings and embodiments hereinafter.

DETAILED DESCRIPTION

Embodiment 1

Step 1: 14.4 g of L-Lactide, 7.6 g of methoxy polyethylene glycol (mPEG) and 0.2 g of stannous iso caprylate were dissolved in 20 mL of dichloromethane to react for 18 hours at 130° C. After that, it was deposited for three times in glacial diethyl ether, and then dried for 3 days at 40° C. under vacuum condition, thus a first intermediate product mPEG-PLA-OH is obtained.

Step 2: 10 g of the first intermediate product mPEG-PLA-OH prepared in step 1, 2 g of butanedioic anhydride and 1.2 g of 4-dimethylaminopyridine were dissolved in 100 mL of chloroform, and 2 mL of triethylamine was added after evenly stirring the mixture. After that, the mixture was first reacted for 3 days at room temperature, then deposited for three times in diethyl ether, filtered and dried for 3 days at 40° C. in vacuum condition, thus a second intermediate product mPEG-PLA-COOH is obtained.

Step 3: 2.5 g of the second intermediate product mPEG-PLA-COOH prepared in step 2 was dissolved in 40 mL of dichloromethane solution, then 0.7 g of 1-ethyl-(3-dimethylamino propyl) carbodiimide hydrochloride and 0.7 g of N-hydroxysuccinimide were added to react for 24 h at room temperature. The mixture was first dissolved in dimethyl sulfoxide solution after rotary evaporation, then added in 60 mL of dimethyl sulfoxide solution which contains 0.5 g of chitosan to react for 24 hours and dialyze for 3 days, and finally the process of freeze-drying was performed to obtain a third intermediate product mPEG-PLA-CS. The dimethyl sulfoxide solution was prepared by mixing dimethyl sulfoxide and water according to a volume ratio of 1:1.

Step 4: 0.5 g of the third intermediate product mPEG-PLA-CS prepared in step 3 was dissolved in 140 mL of water, then 0.3 g of sodium periodate (NaIO4) solution was added. The mixture was incubated for 2 hours at room temperature firstly, and then 300 μL of ethylene glycol was added to react for 2 hours at room temperature and dialyze for 3 days. The process of freeze-drying was finally performed to obtain a fourth intermediate product mPEG-PLA-CS-CHO, and the fourth intermediate product was kept at 4° C. The concentration of the sodium periodate solution was 2.14 g/L.

Step 5: 0.5 g of 5-amino-2-mercapto benzimidazole and 0.2 g of the fourth intermediate product mPEG-PLA-CS-CHO prepared in step 4 were evenly mixed in 40 mL of dimethyl sulfoxide solution, which was prepared by mixing dimethyl sulfoxide and water according to a volume ratio of 1:1. After incubation for 2 hours, 0.2 g of NaCNBH3 was added to react for 48 hours at room temperature. It was then dialyzed for 3 days, and the freeze-drying was performed next, so that thiolated mPEG-PLA-CS-MBI nanoparticles are obtained, and the particles were kept at 4° C.

Figure 3:
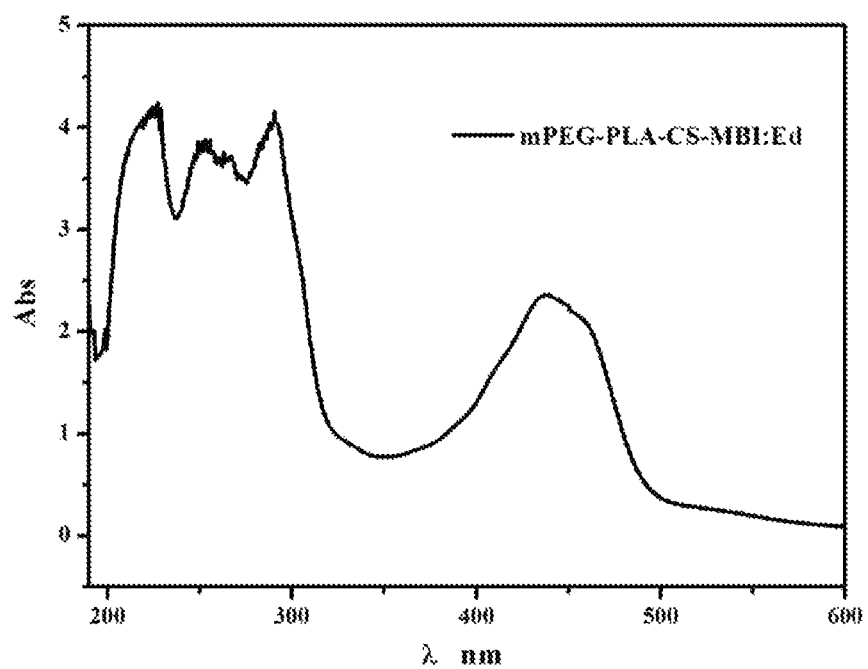
FIG. 3 is an infrared spectrogram of the thiolated mPEG-PLA-CS-MBI nanoparticles prepared in embodiment 1 of the present invention before and after loading emodin.

The mPEG-PLA-CS-MBI nanoparticles prepared in the embodiment were dispersed in deionized water, which can totally disperse, and an ethanol solution dissolved with emodin drugs at a mass concentration of 40% was added. An ultrasound process was performed firstly and then a magnetic stirring process. The mixed solution after stirring was centrifuged at 8000 rpm, and finally, the thiolated guar gum nanoparticles loaded with drugs were frozen to obtain a resulting nano targeted and controlled release system loaded with drugs. FIG. 3 is an infrared spectrogram of the thiolated mPEG-PLA-CS-MBI nanoparticles prepared in this embodiment before and after loading emodin. It can be seen from the figure that, after loading the emodin, there is absorption at 436 nm in FIG. 3, which means that the emodin is successfully loaded on the thiolated mPEG-PLA-CS-MBI nano particles. Finally, after testing, the encapsulation efficiency of the sulfhydrylated thiolated mPEG-PLA- CS-MBI nano particles prepared according to the embodiment after loading the drugs was 91%, and the drug loading capacity was 5.01%.

Figure 1:
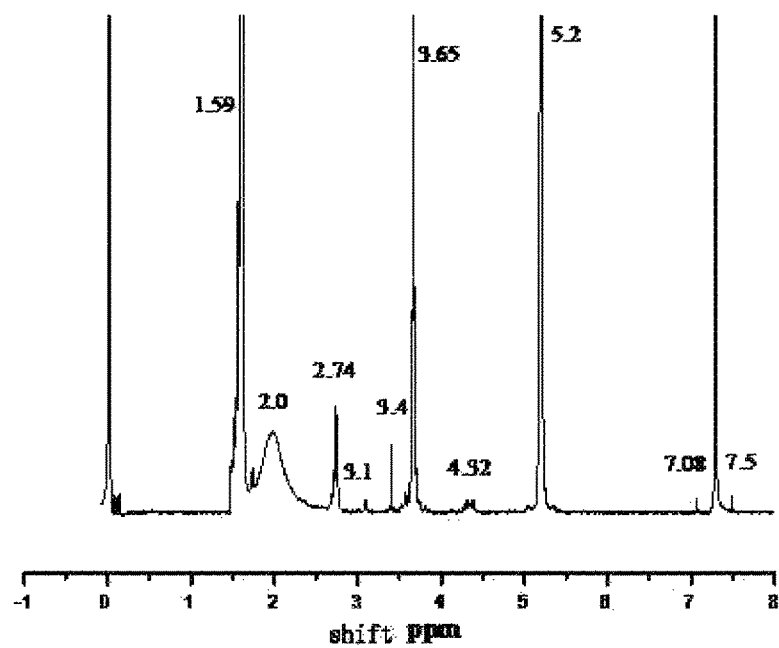
FIG. 1 is an HNMR spectrogram of thiolated mPEG-PLA-CS-MBI nanoparticles prepared in embodiment 1 of the present invention.
Figure 2:
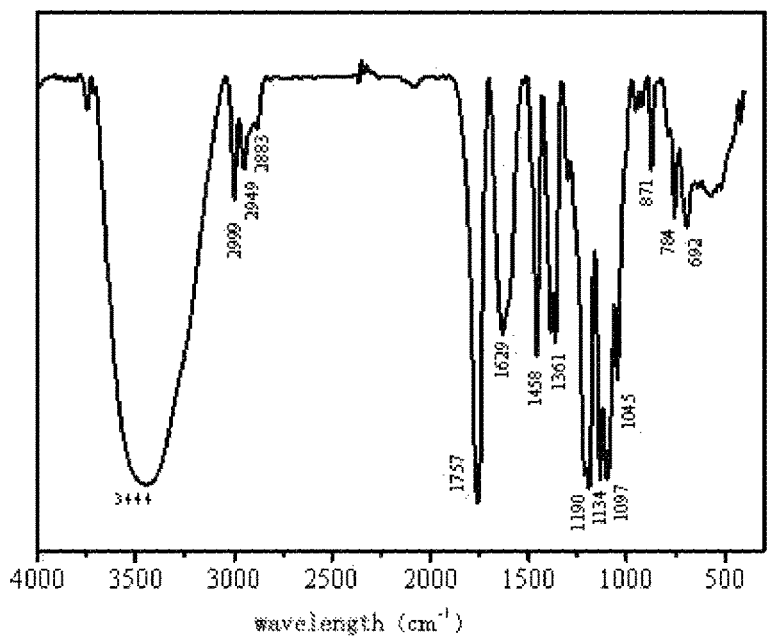
FIG. 2 is a conjugate infrared spectrogram of the thiolated mPEG-PLA-CS-MBI nanoparticles prepared in embodiment 1 of the present invention.

FIG. 1 is an HNMR spectrogram of thiolated mPEG-PLA-CS-MBI nano particles prepared in the embodiment, and FIG. 2 is a conjugate infrared spectrogram of the thiolated mPEG-PLA-CS-MBI nano particles prepared in the embodiment. It can be seen from FIG. 2 that characteristic absorption peaks of the acid amides appear at 1757 cm-1, 1190 cm-1, 1134 cm-1, 1097 cm-1 and 1629 cm-1 respectively, 692 cm-1 and 784 cm-1 show the existence of benzene ring, and are corresponding to the chemical shift at 7.08 ppm and 7.5 ppm in the HNMR spectrogram of FIG. 1. 1458 cm-1 and 1361 cm-1 belong to deformation vibration absorption peaks of —CH3, 2883 cm-1 and 2949 cm-1 are converse stretching vibration absorption peaks of —CH2-, and there is a stronger absorption peak at 3444 cm-1, which is a characteristic stretching vibration absorption peak of NH, and there is only one peak for secondary amine, wherein the absorption peak is stronger, and 1045 cm-1 is a characteristic absorption peak of primary alcohol. The chemical shifts at 3.65 ppm and 5.2 ppm respectively correspond to the positions of hydrogen on the polyethylene glycol and the polylactic acid, which further proves that the modification is successful.

Hydrophilia methoxy polyethylene glycol (mPEG) and polylactic acid (PLA) form an mPEG-PLA-CS polymer in the preparation process of the embodiment, and on this basis, the polymer is thiolated through 5-amino-2-mercapto benzimidazole (MBI) to finally form a thiolated polymer (mPEG-PLA-CS-MBI). The thiolated polymer forms disulfide bonds via thiol oxidation to adhere to the surface of a mucosal membrane, which prolongs residence time of drugs on the mucosal membrane, facilitates the sustained release of drug molecules, and gives enhanced adhesive properties to the thiolated mPEG-PLA-CS-MBI nanoparticles prepared. Meanwhile, after the modified chitosan is combined with the drugs to form a nano-composite, the mPEG may form a core-shell structure micelle on the surface of the composite to prevent the nano-composite from being identified and cleared by the reticuloendothelial system (RES), so that the prepared particles have the surface stabilization effect, which can promote the long circulation of the composite particles in vivo.

Embodiment 2

Step 1: 5 g of L-Lactide (L.A), 2 g of methoxy polyethylene glycol (mPEG) and 0.6 g of stannous iso caprylate were dissolved in 20 mL of dichloromethane to react for 18 hours at 130° C., after that the process that depositing for three times in glacial diethyl ether was performed, and then the process that drying for 3 days at 40° C. under vacuum condition was performed to obtain a first intermediate product mPEG-PLA-OH.

Step 2: 10 g of the first intermediate product mPEG-PLA-OH prepared in step 1, 2 g of butanedioic anhydride and 1.2 g of 4-dimethylaminopyridine were dissolved in 100 mL of chloroform, and 2 mL of triethylamine was added after evenly stirring the mixture to react for 3 days at room temperature. After that, the process that depositing for three times in diethyl ether was first performed, and then the filtering process, and finally the process that drying for 3 days at 40° C. in vacuum condition was performed to obtain a second intermediate product mPEG-PLA-COOH.

Step 3: 2.5 g of the second intermediate product mPEG-PLA-COOH prepared in step 2 was dissolved in 40 mL of dichloromethane, then 0.7 g of 1-ethyl-(3-dimethylamino propyl) carbodiimide hydrochloride and 0.7 g of N-hydroxysuccinimide were added to react for 24 hours at room temperature, the mixture was dissolved in dimethyl sulfoxide solution after rotary evaporation, then added in 60 mL of dimethyl sulfoxide solution which contains 0.5 g of chitosan to react for 24 hours and dialyze for 3 days. The process of freeze-drying was finally performed to obtain a third intermediate product mPEG-PLA-CS. The dimethyl sulfoxide solution was prepared by mixing dimethyl sulfoxide and water according to a volume ratio of 1:1.

Step 4: 0.5 g of the third intermediate product mPEG-PLA-CS prepared in step 3 was dissolved in 140 mL of water, then 0.3 g of sodium periodate (NaIO4) solution was added. The process that incubating for 2 hours at room temperature was first performed, and 300 μL of ethylene glycol was added to react for 2 hours at room temperature and dialyze for 3 days, and then the process of freeze-drying was performed to obtain a fourth intermediate product mPEG-PLA-CS-CHO, and the fourth intermediate product was kept at 4° C. The concentration of the sodium periodate solution was 2.14 g/L.

Step 5: 0.2 g of 5-amino-2-mercapto benzimidazole (MBI) and 0.2 g of the fourth intermediate product mPEG-PLA-CS-CHO prepared in step 4 were evenly mixed in 40 mL of dimethyl sulfoxide solution, and after the process that incubating for 2 hours at room temperature was performed, 0.5 g of NaCNBH3 was added to react for 24 hours at room temperature. The process that dialyzing for 3 days was then performed, and finally the process of freeze-drying was performed to obtain thiolated mPEG-PLA-CS-MBI nanoparticles, and the particles were kept at 4° C. The dimethyl sulfoxide solution was prepared by mixing dimethyl sulfoxide and water according to a volume ratio of 1:1.

The mPEG-PLA-CS-MBI nano particles prepared in the embodiment were dispersed in deionized water, which can be completely dispersed, and an ethanol solution dissolved with emodin drug at a concentration of 40% was added, then the ultrasound process was performed. After that, magnetic stirring was performed, and then the mixed solution after stirring was centrifuged at 8000 rpm, and finally, thiolated guar gum nanoparticles loaded with drugs were frozen to obtain a final nano targeted and sustained release system loaded with drugs. After examination, the encapsulation efficiency of the thiolated mPEG-PLA-CS-MBI nanoparticles, prepared according to the embodiment, after loading the drugs was 86.3%, and the drug loading capacity was 4.11%.

Embodiment 3

Step 1: 20 g of L-Lactide, 10 g of methoxy polyethylene glycol (mPEG) and 1 g of stannous iso caprylate were dissolved in 20 mL of dichloromethane. After reacting for 18 hours at 130° C., the process that depositing for three times in glacial diethyl ether was performed, and then the process that drying for 3 days at 40° C. in vacuum condition was performed to obtain a first intermediate product mPEG-PLA-OH.

Step 2: 10 g of the first intermediate product mPEG-PLA-OH prepared in step 1, 2 g of butanedioic anhydride and 1.2 g of 4-dimethylaminopyridine were dissolved in 100 mL of chloroform, and 2 mL of triethylamine was added after being evenly stirred. The process that reacting for 3 days at room temperature was first performed, and the process that depositing for three times in diethyl ether was next performed, and then the filtering process, and finally the process that drying for 3 days at 40° C. in vacuum condition was performed to obtain a second intermediate product mPEG-PLA-COOH.

Step 3: 2.5 g of the second intermediate product mPEG-PLA-COOH prepared in step 2 was dissolved in 40 mL of dichloromethane, then 0.7 g of 1-ethyl-(3-dimethylamino propyl) carbodiimide hydrochloride and 0.7 g of N-hydroxysuccinimide were added to react for 24 hours at room temperature. The mixture was first dissolved in dimethyl sulfoxide solution after rotary evaporation. and then added in 60 mL of dimethyl sulfoxide which contains 0.5 of chitosan to react for 24 hours and dialyze for 3 days. Finally, the process of freeze-drying was performed to obtain a third intermediate product mPEG-PLA-CS. The dimethyl sulfoxide solution was prepared by mixing dimethyl sulfoxide and water according to a volume ratio of 1:1.

Step 4: 1 g of the third intermediate product mPEG-PLA-CS prepared in step 3 was dissolved in 140 mL of water, then 0.3 g of sodium periodate (NaIO4) solution was added. The process that incubating for 2 hours at room temperature was first performed, then 300 μL of ethylene glycol was added to react for 2 hours at room temperature and dialyze for 3 days, and finally the process of freeze-drying was performed to obtain a fourth intermediate product mPEG-PLA-CS-CHOl, and the fourth intermediate product was kept at 4° C. The concentration of the sodium periodate solution was 2.14 g/L.

Step 5: 1 g of 5-amino-2-mercapto benzimidazole (MBI) and 0.2 g of the fourth intermediate product mPEG-PLA-CS-CHO prepared in step 4 were evenly mixed in 40 mL of dimethyl sulfoxide solution, which was prepared by mixing dimethyl sulfoxide and water according to a volume ratio of 1:1. After incubation for 2 hours at room temperature, 2 g of NaCNBH3 was added to react for 72 hours at room temperature and dialyze for 3 days, and then the process of freeze-drying was performed to obtain thiolated mPEG-PLA-CS-MBI nano particles, and the particles were kept at 4° C.

The mPEG-PLA-CS-MBI nano particles prepared in the embodiment were dispersed in deionized water, which can be completely dispersed, and an ethanol solution dissolved with 40% emodin drug was added, then ultrasound processing was performed. After that, magnetic stirring was performed, then the mixed solution after stirring was centrifuged at 8000 rpm, and finally, thiolated guar gum nano particles loaded with drugs were frozen to obtain a final nano targeted and sustained release system loaded with drugs. According to the test, the encapsulation efficiency of the thiolated mPEG-PLA-CS-MBI nano particles, prepared according to the embodiment, after loading the drugs was 83.6%, and the drug loading capacity was 3.89%.

The contents above are only preferable embodiments of the invention, but are not intended to limit the invention. Any simple amendment, alteration and equivalent change made to the embodiments above according to the technical substance of the invention shall all fall within the protection scope of the technical solution of the invention.

The invention claimed is:

1. A preparation method of nanoparticles for loading emodin characterized in that the method comprises the following steps:
   step 1: dissolving 5 g-20 g of L-Lactide, 2 g-10 g of methoxy polyethylene glycol and 0.2 g-1 g of stannous iso caprylate in 20 mL of dichloromethane, placing the mixture into glacial diethyl ether to deposit for three times after reacting for 18 hours at 130° C., and then drying the mixture for 3 days at 40° C. in vacuum condition to obtain a first intermediate product mPEG-PLA-OH;
   step 2: dissolving 10 g of the first intermediate product mPEG-PLA-OH prepared in step 1, 2 g of butanedioic anhydride and 1.2 g of 4-dimethylaminopyridine in 100 mL of chloroform, adding 2 mL of triethylamine after evenly stirring the mixture, reacting for 3 days at room temperature, then placing the mixture in diethyl ether to deposit for three times, performing a filtration process to obtain filter residues, drying the filter residues for 3 days at 40° C. in vacuum condition to finally obtain a second intermediate product mPEG-PLA-COOH;
   step 3: dissolving 2.5 g of the second intermediate product mPEG-PLA-COOH prepared in step 2 in 40 mL of dichloromethane, then adding 0.7 g of 1-ethyl-(3-dimethylamino propyl) carbodiimide hydrochloride and 0.7 g of N-hydroxysuccinimide to react for 24 hours at room temperature, dissolving the mixture in dimethyl sulfoxide solution after rotary evaporation, then adding the mixture in 60 mL of dimethyl sulfoxide added with chitosan to react for 24 hours, dialyzing for 3 days, and performing a freeze-drying process to obtain a third intermediate product mPEG-PLA-CS; wherein the additive amount of the chitosan is between 0.1 g-1 g, with boundary values included, and the deacetylation degree is 85%;
   step 4: dissolving 0.5 g of the third intermediate product mPEG-PLA-CS prepared in step 3 in 140 mL of water, then adding 0.3 g of sodium periodate solution to incubate for 2 hours at room temperature, then adding 300 μL of ethylene glycol to react for 2 hours at room temperature, dialyzing for 3 days, and performing the process of freeze-drying to obtain a fourth intermediate product mPEG-PLA-CS-CHO and keeping the fourth intermediate product at 4° C., wherein the concentration of the sodium periodate solution is 2.14 g/L; and
   step 5: dissolving 0.2 g-1 g of 5-amino-2-mercapto benzimidazole and 0.2 g of the fourth intermediate product mPEG-PLA-CS-CHO prepared in step 4 in 40 mL of dimethyl sulfoxide solution and incubating for 2 hours at room temperature, then adding 0.2 g-2 g of sodium cyanoborohydride to react for 24 h to 72 h at room temperature, dialyzing for 3 days, and performing the process of freeze-drying to obtain thiolated mPEG-PLA-CS-MBI nanoparticles used for loading emodin and keeping the nanoparticles at 4° C.;
   both the dimethyl sulfoxide solution in step 3 and the dimethyl sulfoxide solution in step 5 being prepared by mixing dimethyl sulfoxide with water according to a volume ratio of 1:1.

2. The preparation method of nanoparticles for loading emodin according to claim 1 wherein the average molecular weight of the ethylene glycol monomethyl ether in step 1 is between 1000-4000, with boundary values included.

3. The preparation method of nanoparticles for loading emodin according to claim 1 wherein the mass of the L-Lactide in step 1 is 14.4 g, the mass of the methoxy polyethylene glycol is 7.6 g, and the mass of the stannous iso caprylate is 0.2 g.

4. The preparation method of nanoparticles for loading emodin according to claim 1 wherein the additive amount of the chitosan in step 3 is 0.5 g.

5. The preparation method of nanoparticles for loading emodin according to claim 1 wherein the mass of the 5-amino-2-mercapto benzimidazole in step 5 is 0.5 g.

6. The preparation method of nanoparticles for loading emodin according to claim 1 wherein the mass of the sodium cyanoborohydride added in step 5 is 0.2 g.

7. The preparation method of nanoparticles for loading emodin according to claim 1 wherein the reaction time in step 5 is 48 hours.

\* \* \* \* \*